(12) United States Patent
Makey

(10) Patent No.: US 10,905,447 B2
(45) Date of Patent: Feb. 2, 2021

(54) SPECIMEN REMOVAL DEVICE

(71) Applicant: Ian Makey, San Antonio, TX (US)

(72) Inventor: Ian Makey, San Antonio, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 15/127,325

(22) PCT Filed: Mar. 21, 2015

(86) PCT No.: PCT/US2015/021902
§ 371 (c)(1),
(2) Date: Sep. 19, 2016

(87) PCT Pub. No.: WO2015/143422
PCT Pub. Date: Sep. 24, 2015

(65) Prior Publication Data
US 2017/0181767 A1    Jun. 29, 2017

Related U.S. Application Data

(60) Provisional application No. 61/968,468, filed on Mar. 21, 2014.

(51) Int. Cl.
*A61B 17/221* (2006.01)
*A61B 17/00* (2006.01)

(52) U.S. Cl.
CPC ...... *A61B 17/221* (2013.01); *A61B 17/00234* (2013.01); *A61B 2017/00287* (2013.01)

(58) Field of Classification Search
CPC ............................................ A61B 2017/00287
USPC ........................................................ 606/114
See application file for complete search history.

(56) References Cited

U.S. PATENT DOCUMENTS

| | | | | |
|---|---|---|---|---|
| 5,788,709 A | * | 8/1998 | Riek | A61B 17/00234 |
| | | | | 606/110 |
| 6,270,505 B1 | * | 8/2001 | Yoshida | A61B 17/00234 |
| | | | | 606/127 |
| 8,172,772 B2 | | 5/2012 | Zwolinski et al. | 600/562 |
| 8,579,914 B2 | | 11/2013 | Menn et al. | 606/114 |
| 2012/0083795 A1 | * | 4/2012 | Fleming | A61B 17/00234 |
| | | | | 606/114 |

(Continued)

OTHER PUBLICATIONS

International Preliminary Report on Patentability in International Application No. PCT/US2015/021902 dated Sep. 29, 2016.

(Continued)

*Primary Examiner* — Melanie R Tyson
(74) *Attorney, Agent, or Firm* — Norton Rose Fulbright US LLP

(57) ABSTRACT

Certain embodiments are directed to a specimen retrieval device having a high friction inner lining for reducing specimen deformation during removal. Certain embodiments are directed to a device that facilitates isolation and removal of specimens during minimally invasive surgery. In certain aspects the device is configured to disperse pulling tension over a larger area reducing the likelihood of specimen tearing during removal. The device enables quicker removal through a smaller hole or opening in the body wall.

8 Claims, 7 Drawing Sheets

(56) References Cited

U.S. PATENT DOCUMENTS

2012/0158010 A1* 6/2012 Menn ............... A61B 17/00234
                                                         606/114
2013/0116592 A1   5/2013 Covidien ...................... 600/562

OTHER PUBLICATIONS

International Search Report and Written Opinion in International Application No. PCT/US2015/021902 dated Jul. 6, 2015.

* cited by examiner

Body Exterior

Body Cavity

SPECIMEN REMOVAL DEVICE

This application is a national phase application under 35 U.S.C. § 371 of International Application No. PCT/US2015/021902, filed Mar. 21, 2015 which claims priority to U.S. Provisional Patent Application Ser. No. 61/968,468, filed Mar. 21, 2014. Both applications are hereby incorporated in their entirety.

BACKGROUND

The field of minimally invasive surgery has become commonplace. Large specimens are being resected using minimally invasive techniques. The limitation to removing these larger specimens is the port size. The current method to remove a specimen is to put it into a laparoscopic endocatch bag and withdraw it from the body cavity. This method of extraction causes the specimen to bunch at the bottom of the bag. Extra force or a larger hole is required to complete extraction. There is a need for additional devices for removing a specimen from a body cavity.

SUMMARY

Certain embodiments are directed to a device that facilitates isolation and removal of specimens during minimally invasive surgery. In certain aspects the device is configured to disperse pulling tension over a larger area reducing the likelihood of specimen tearing during removal. The device enables quicker removal through a smaller hole or opening in the body wall.

The device is designed to reduce bunching of the specimen during removal by providing an area of high friction or a one-way friction. The bunching of a specimen bag increases the size of the incision needed to remove the specimen. Embodiments of the device described herein can minimize the size of the incision required to extract the specimen. In certain aspects the device can be re-used within the same operation, for example if multiple specimens need to be removed. Certain embodiments are directed to a device having two openings, a distal opening for retrieving the specimen and a proximal opening for access to the body cavity. In certain aspects the device comprises a high friction material or a one-way friction inner lining that distributes tension along a broad area of the specimen. The device can be used to remove specimens from a body cavity that have been resected using minimally invasive techniques. In certain respects a constricting force on the specimen can be generated during the traversal of the chest wall. The constrictive force generated by withdrawing the specimen through the chest wall increases the coefficient of friction between the specimen and the high friction or one-way friction liner.

Certain embodiments are directed to a specimen retrieval device comprising a flexible elongated body forming an enclosed channel or lumen along the long axis of the device, which has an inner surface and an external surface, that is configured to traverse an opening in the body wall of a subject; the elongated body having (i) a top portion with a neck and rim configured to be positioned proximal and external to an opening in a subject's body wall; (ii) a bottom portion configured to receive a specimen into the channel or lumen formed by the elongated body and configured to be positioned in a body cavity. In certain aspects all or a portion of the inner surface of the channel comprises a high friction or a one-way friction liner.

Certain embodiments are directed to a specimen retrieval device comprising a flexible elongated body forming an enclosed channel along the long axis of the device that is configured to traverse an opening in the body wall of a subject; the elongated body having (i) a top portion with a neck and rim configured to be positioned proximal and external to an opening in a subject's body wall; (ii) a bag portion distal to the top portion; (iii) a specimen receiving portion positioned between the top portion and bag portion that is configured to span an opening formed in the body wall of a subject, the specimen receiving portion comprising a specimen securing area, wherein the specimen securing area is configured to contact a specimen and resist the movement of the specimen back into the subject.

In certain aspects the neck and rim is configured to facilitate access to the body cavity. The ring and neck can provide for insertion of instruments via the lumen of the device.

In certain aspects the inner surface of the specimen securing area is textured forming a high friction surface. The texture can be a grid, a geometric pattern, or an irregular surface similar to sandpaper. In further aspects the specimen securing area comprises a plurality of surface protrusions. The surface protrusions can be present in a density of at most, at least, or about 0.1, 1, 10, 100, 1000, 10,000, 100,000, 1000,000 protrusions per $mm^2$, including all values and ranges there between. The surface protrusion can have an outer edge that is proximal to the bag portion or distal end, and an inner edge that is proximal to the top portion or proximal end. Referring to FIG. 5 as an example, in certain aspects outer angle 501 formed between the specimen receiving portion surface and the exterior edge of the protrusion is at least 90, 100, 110, 120, 130, 140, 150, 160, 170 degrees, including all values and ranges there between. In certain aspects the angle is greater than 100 degrees. In a further aspect inner angle 502 formed between the specimen receiving portion surface and the interior edge of the protrusion is at least 90, 100, 110, 120, 130, 140, 150, 160, 170 degrees, including all values and ranges there between. In certain aspects the angle formed between the specimen receiving portion surface and the exterior edge of the protrusion is greater than 135 degrees. In a further aspect the angle formed between the specimen receiving portion surface and the exterior edge of the protrusion is greater than 160 degrees. The protrusion can be an irregular protrusion, a fiber (approximately cylindrical in shape), a wedge, a pyramid, a barb, a spike, a hook, or a loop. The protrusion can have cross section parallel to the inner surface that is circular, elliptical, oblong, triangular, square, rectangular, rhomboid, trapazoid, diamond, or other geometric shape. In certain respect the wedge can have a pointed, straight, or curved edge. A curved edge can curve out from the wedge or in towards the wedge. The curve can be semicircular to elliptical (similar to a cheese grater). In a further aspect the edge is sharp so that it can penetrate the surface of a sample. In certain respects the protrusion can have a height (see height 503 of FIG. 5 for an example) of 0.5, 5, 50, 100, 500 µm to 1, 2, 3, 4, 5 mm, including all values and ranges there between. The protrusion can have width or diameter (see width 504 of FIG. 5 for an example) of 0.5, 5, 50, 100, 500 µm to 1, 2, 3, 4, 5 mm, including all values and ranges there between. The width or diameter can change or taper along the height, the length, or the height and the length of the protrusion. The protrusion can have a length (see length 505 of FIG. 5 for an example) of 0.5, 5, 50, 100, 500 µm to 1, 2, 3, 4, 5 mm, including all values and ranges there between. In certain respects the width refers to the cross section of the protrusion at the base with various configurations changing width, length of width and length along the height of the protrusion, e.g., the protrusion can taper as one moves from base to tip or edge. In certain respects the protrusion or texture is molded, embossed, or etched onto or into the surface.

In certain aspects a device can further comprise a constrictor element associated with the bag portion that can be in an engaged or disengaged configuration, wherein the constrictor can be engaged once a sample is in contact with the specimen receiving portion and further inhibits movement of the specimen back towards the subject. The specimen receiving portion can comprise at least one elastic band or is formed from an elastic material that is configured to provide pressure on the specimen when it is moved into the specimen receiving portion. The pressure provided can assist in engaging the protrusions of the specimen securing area. In certain respect the inward pressure of the body wall will provide pressure on the specimen and the device. In certain aspects the coefficient of friction, with or without the elastic band, is enhanced by the tangential force between the specimen, the wall of the device, and the inner circumference of the incision.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DESCRIPTION

Embodiments of the specimen removal device described herein include an impermeable, cylindrical body. In certain aspects the body is a plastic sheeting or similar flexible material that can be folded. The device is configured to allow a portion of the folded device to be inserted in a body cavity through an incision. Once inserted the device can be deployed such that it traverses the body wall and provides an access channel though which instruments can be introduced into a body cavity and tissues can be removed.

The device has an interior surface and an exterior surface. In certain aspects the device has a reduced or low friction exterior surface. In a further aspect the interior surface of the device has one or more specimen receiving segments or portions having a surface region(s) that provide an increased resistance to specimen movement (high friction region). In certain embodiments the movement resistance surface regions of the specimen receiving segment or portion is directional in that movement of a specimen into the specimen receiving segment or portion experiences minimal resistance in one direction whereas the movement in the opposite direction, i.e., back towards the opening of the device in the body cavity where the specimen enters the lumen of the device, is resisted.

There are several different manufacturing approaches to produce a segment having a directional resistance. The first is providing a plurality of short hairs at an angle. In certain aspects the hairs or fibers can be nanoscale hairs or fibers—this material is used for ski climbing skins. Another approach is to use indentions or protrusions from the plastic itself to produce a "hook and glide" surface.

Having a directionally resistant surface allows the specimen to slide through the device in one direction only. Therefore the specimen is pulled into the device in a pre-specified direction. The specimen can be grasped by an instrument positioned through or in the lumen of the device. Resistance will increase as the specimen is pulled into the incision. Once the specimen is in an appropriate position for removal tension is applied to the device. The tension applied to the specimen by pulling the device is distributed over a broader area of the specimen to prevent tearing or bunching of the specimen. The directional resistance helps maintain specimen location and inhibits the movement of the specimen back into the body cavity.

Figure 1A:
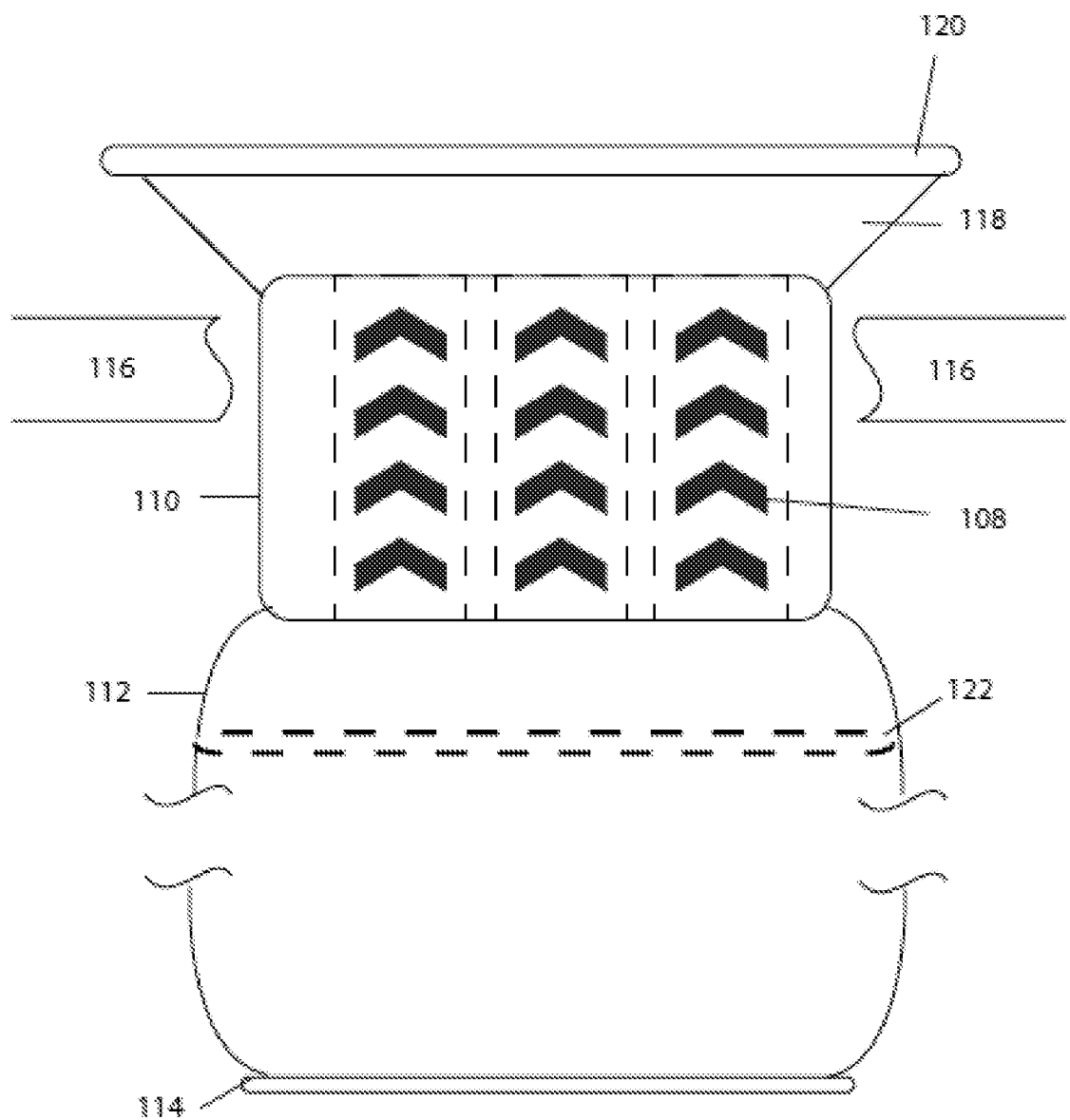
FIG. 1A-1C. (A) Illustrates a cross section of one embodiment of a specimen bag positioned in the body wall of a subject. (B) Three dimensional illustration of FIG. 1A. (C) Illustration of an alternative embodiment of the specimen removal device.
Figure 1B:
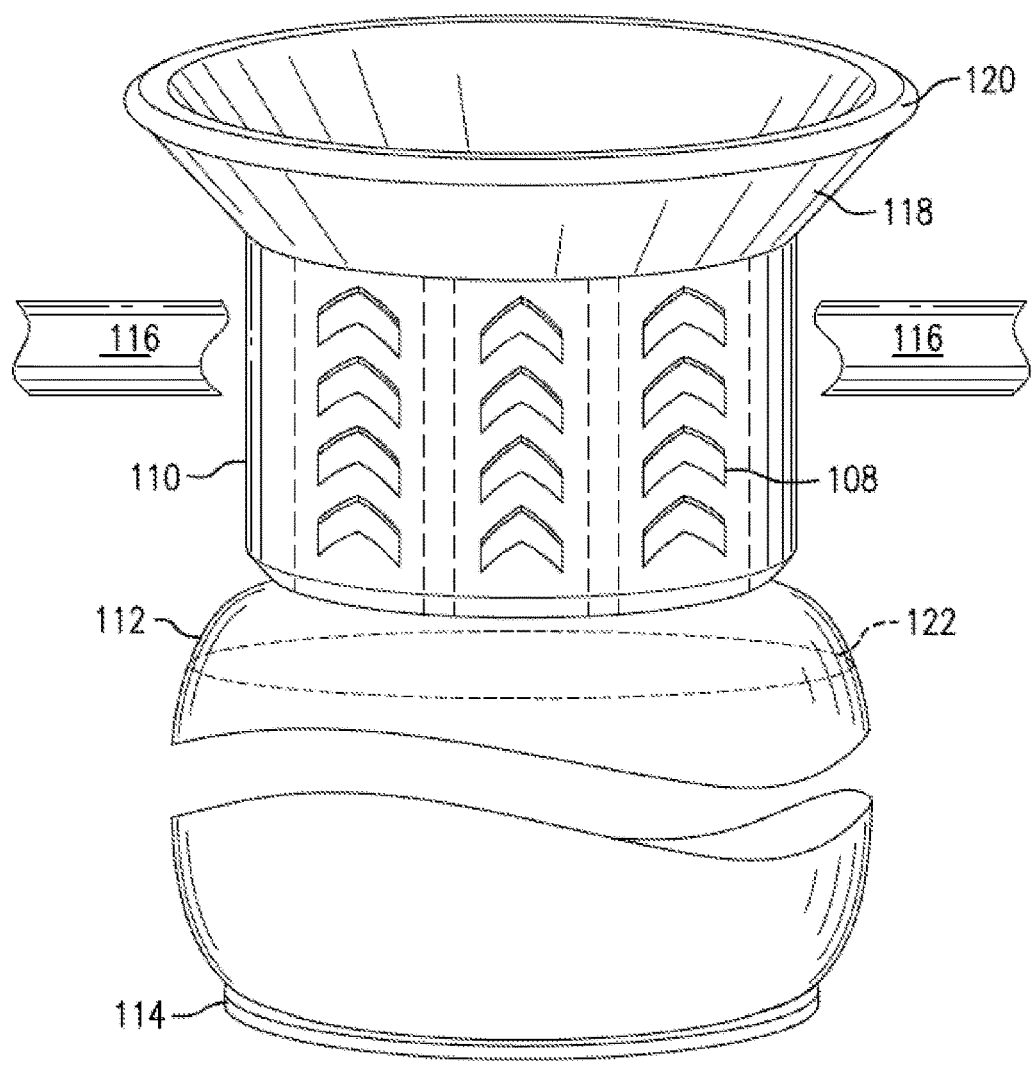
Figure 1C:
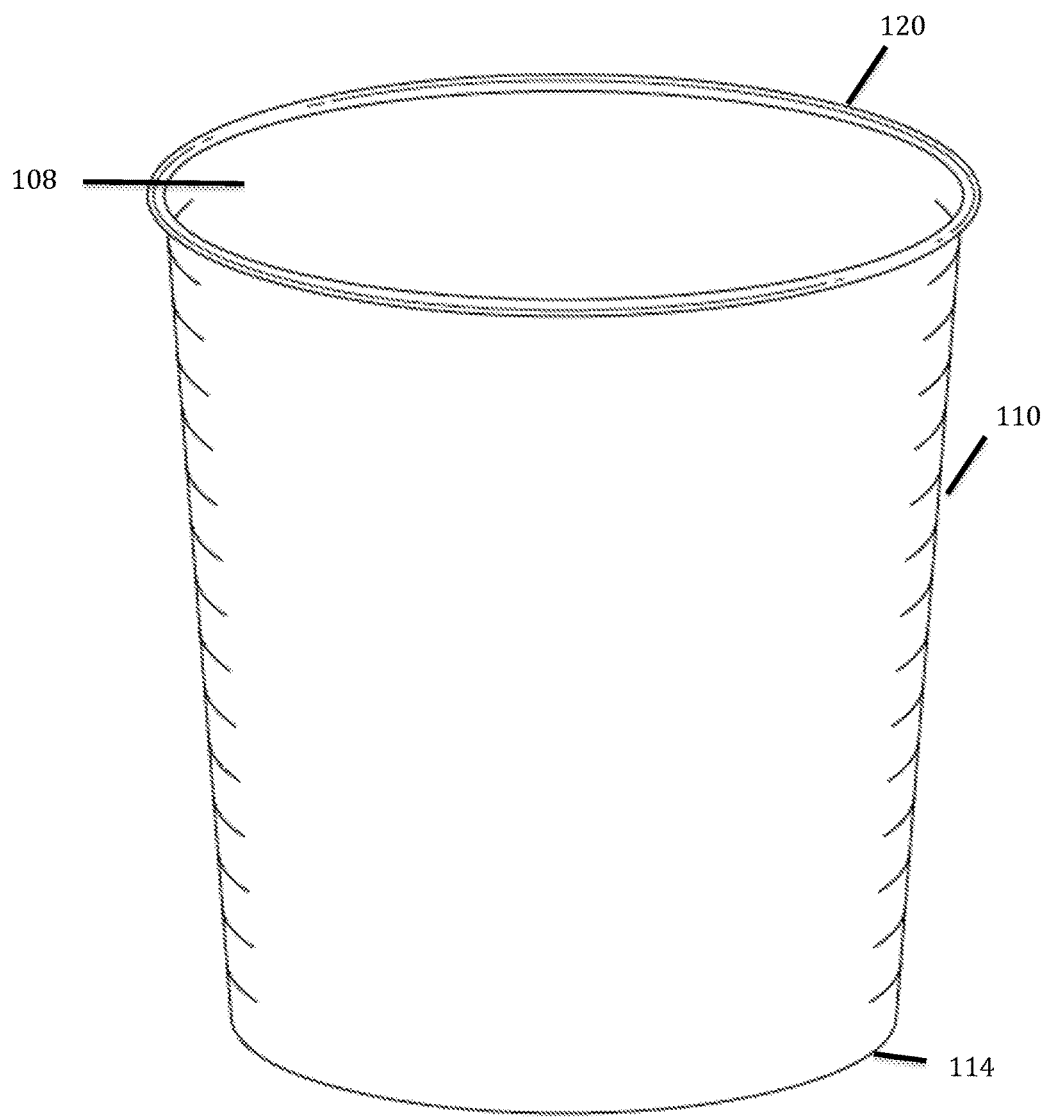
Figure 2:
FIG. 2. Illustrates one embodiment of a directionally resistant surface using hair like protrusions.
Figure 2:
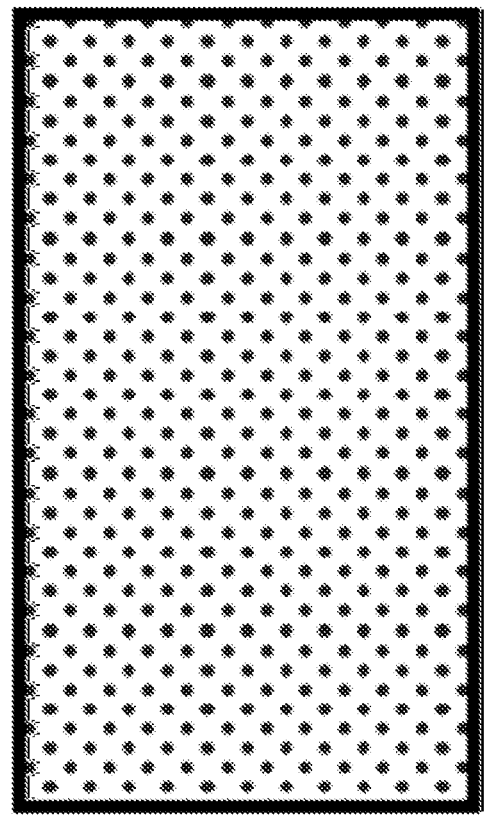
Figure 3:
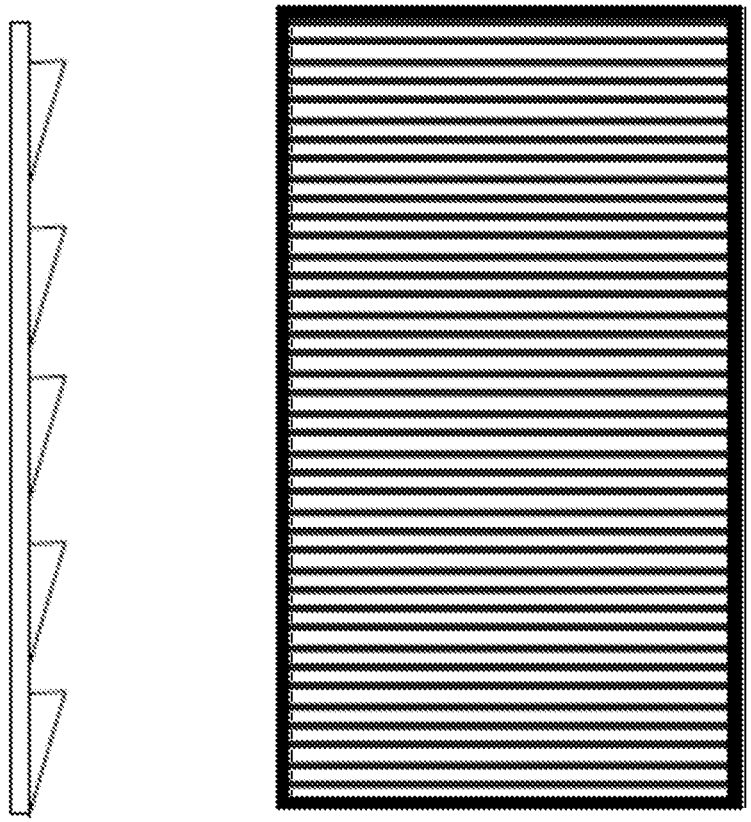
FIG. 3. Illustrates one embodiment of a directionally resistant surface using slide and catch protrusions.
Figure 4:
FIG. 4. Illustrates one embodiment of a directionally resistant surface using directional hook protrusions.
Figure 4:
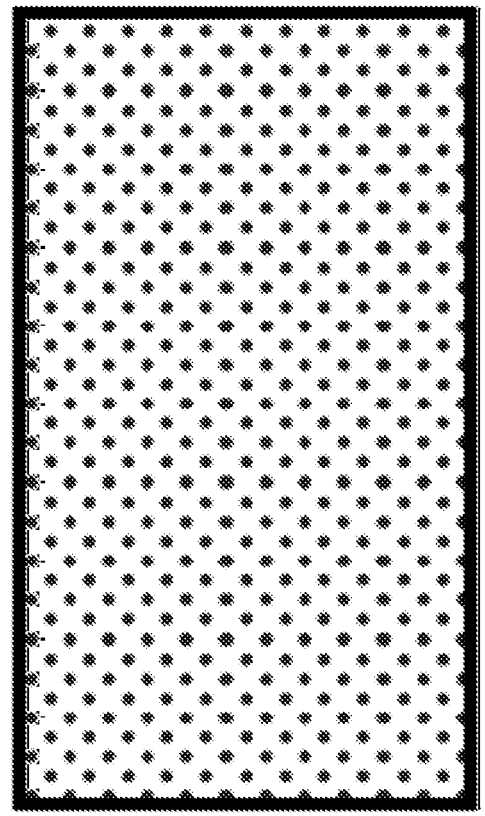
Figure 5:
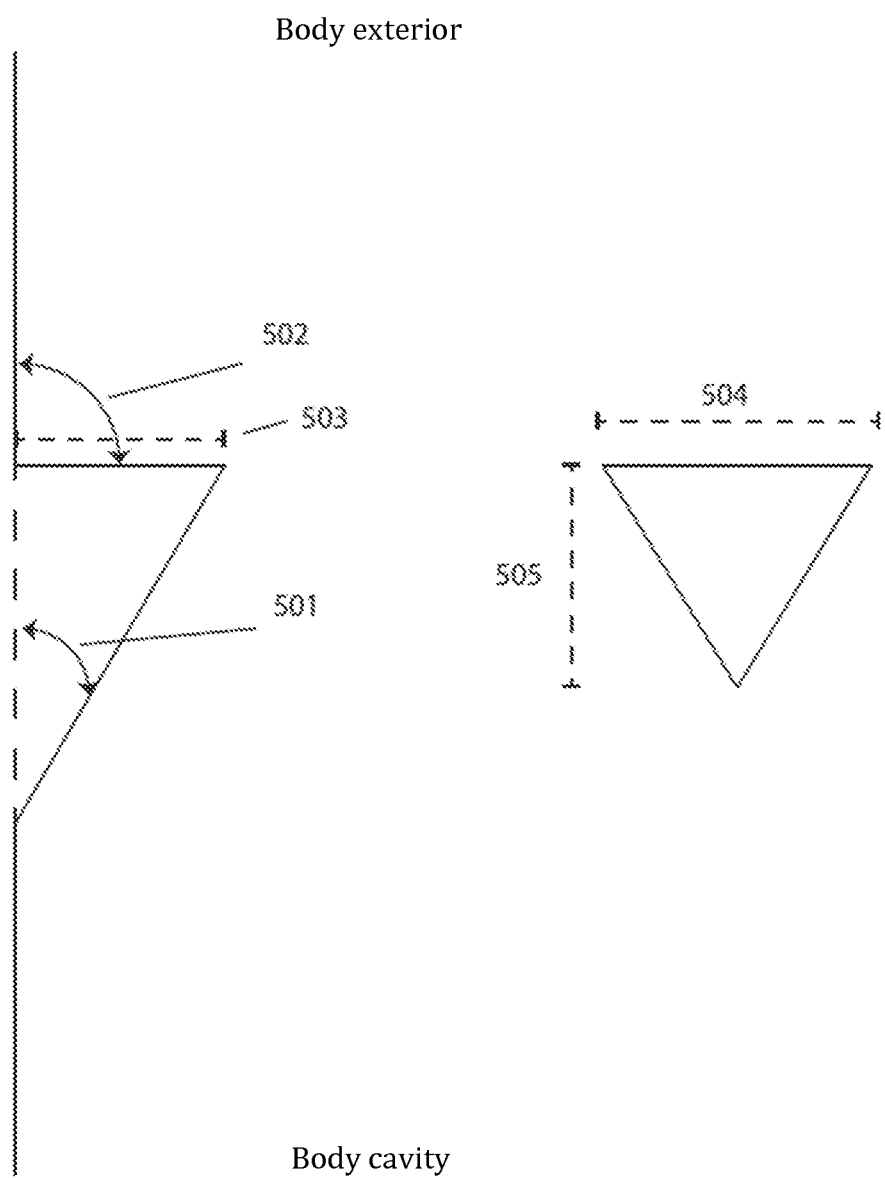
FIG. 5. Illustrates an example of a protrusion and angles and measurements for characterizing the three-dimensional shape of the protrusion.

Certain embodiments are directed to a device for assisting in the removal of a specimen from a body cavity. FIGS. 1A and 1B illustrates one embodiment of such a device. With reference to FIG. 1, a device can be configured to be position in body wall 116 of a subject having an external portion (rim 120 and sleeve 118) that is generally outside of a subject, a transverse portion traversing body wall 116 having a specimen receiving portion 110, and an internal portion in the subject's body cavity (bag 112 and seal 114). In certain aspect 114 can be substituted by a flexible ring. In certain aspects bag 112 can include constriction ring 122 to provide support to the bottom of a specimen moved into position for removal. In certain embodiments the internal portion can be long enough so that once a specimen is positioned in the device the distal end of the internal portion can be pulled though a second incision. In certain aspects the internal portion pulled through the second incision can be secured or sealed.

The external portion is configured to secure the device externally with respect to a subject undergoing surgery. The external portion also provides a pull point(s) in removing a specimen positioned in the device or removing the device. In certain aspects fiber or strands of reinforcing material can be included in the wall to strengthen the device and resist tearing while providing for the application of enough force to remove the specimen and device from the body. In certain aspects handles are included in the external portion of the device for pulling the device. The handles can be configured to dissipate the pulling force over the perimeter of the device.

Specimen receiving portion 110 comprises a portion of the interior surface having a specimen securing area(s) 108 that are configured to assist in specimen removal from the body cavity. In certain aspects specimen securing area 108 comprises a textured inner surface forming a high friction inner surface. The specimen receiving portion 110 is configured to resist movement of the specimen from the receiving portion to the body cavity, in other words it prevents the specimen slipping back into the body. In certain aspects these directional friction areas comprise protrusions that originate at the surface of specimen receiving portion 110 and project towards the external surface of a subjects body. In certain aspects the protrusions are short hair-like protrusions, wedge protrusions, loop protrusions, or the like. In certain aspects the body cavity side of the protrusion forms an acute angle with respect to the wall of specimen receiving portion 110 and the edge of the protrusion on the body cavity side of the protrusion. The vertex of the formed angle is positioned proximal to specimen bag 112. In certain aspects the angle between the protrusion and the specimen receiving portion is about 60, 55, 50, 45, 40, 35, 30, or so degrees. The protrusions are configured so that when in contact with an incoming specimen movement of the specimen from the bag portion to the specimen receiving portion is favored, which allows the specimen to move into the specimen receiving portion, and movement of the specimen back into the bag or body cavity is resisted. In certain aspects receiving portion 110 is configured to provide an elastic, constrictive force to the specimen as well as the directional resistance.

Seal 114 is designed to act as a semi-rigid handle to facilitate moving the tubing over the specimen. This would be a two instrument technique in which the specimen is pulled into the bag with one instrument and the bag would be pushed over and around the specimen with another instrument. Having a semi-rigid handle would facilitate enclosure of the specimen with the tubing.

Seal 114 is also designed to contain any fluid or debris that may be discharged from the specimen as it is squeezed and withdrawn from the body. In certain aspects the seal is designed so that a water tight seal can be formed in the cavity of a subject prior to removal of the specimen. The seal can be formed by a drawstring, an adhesive, a heat seal, a snap, a clip, a zip lock mechanism, a slide lock mechanism, interlocking edges, etc.

The examples as well as the figures are included to demonstrate certain but not all embodiments of the invention. It should be appreciated by those of skill in the art that the techniques and devices disclosed in the examples or figures represent techniques and devices discovered by the inventors to function well in the practice of the invention, and thus can be considered to constitute preferred but not required modes for its practice. However, those of skill in the art should, in light of the present disclosure, appreciate that many changes can be made in the specific embodiments which are disclosed and still obtain a like or similar result without departing from the spirit and scope of the invention.

The invention claimed is:

1. A specimen retrieval device comprising
a flexible elongated body forming a channel along a long axis of the device, the device having a proximal opening and a distal opening and configured to traverse an opening in a body wall of a subject and configured to provide an access channel through which an instrument for specimen removal can be introduced into a body cavity;
the elongated body having (i) a top portion with a neck and rim configured to be positioned proximal and external to an opening in a subject's body wall; (ii) a specimen receiving portion configured to span an opening formed in the body wall of a subject, the specimen receiving portion comprising a specimen securing area, wherein the specimen securing area has a directionally resistant inner surface comprising a plurality of surface protrusions configured to contact a specimen, the specimen receiving portion configured to allow movement of the specimen into the specimen receiving portion but resist movement of the specimen back into the subject.

2. The specimen retrieval device of claim 1, further comprising a bag portion distal to the top portion and the specimen receiving portion.

3. The device of claim 2, further comprising a constrictor element associated with the bag portion that can be in an engaged or disengaged configuration, wherein the constrictor element can be engaged once a sample is in contact with the specimen receiving portion and further inhibits movement of the specimen back towards the subject.

4. The device of claim 1, wherein the surface protrusions have an outer edge that is proximal to the bag portion and an inner edge that is proximal to the top portion and an angle formed between a surface of the specimen receiving portion and an exterior edge of the protrusion is greater than 100 degrees.

5. The device of claim 4, wherein the angle formed between the surface of the specimen receiving portion and the exterior edge of the protrusion is greater than 135 degrees.

6. The device of claim 4, wherein the angle formed between the surface of the specimen receiving portion and the exterior edge of the protrusion is greater than 160 degrees.

7. The device of claim 1, wherein the plurality of surface protrusions are a wedge, a spike, a barb, a hook, or a loop.

8. The device of claim 1, wherein the specimen receiving portion comprises at least one elastic band or is formed from an elastic band.

* * * * *